US005705478A

United States Patent [19]

Boime

[11] Patent Number: 5,705,478
[45] Date of Patent: Jan. 6, 1998

[54] COVALENTLY LINKED β SUBUNITS OF THE GLYCOPROTEIN HORMONES AS ANTAGONISTS

[75] Inventor: Irving Boime, St. Louis, Mo.

[73] Assignee: Washington University, St. Louis, Mo.

[21] Appl. No.: 334,628

[22] Filed: Nov. 4, 1994

Related U.S. Application Data

[63] Continuation-in-part of Ser. No. 310,590, Sep. 22, 1994, which is a continuation-in-part of Ser. No. 289,396, Aug. 12, 1994, which is a continuation-in-part of Ser. No. 49,869, Apr. 20, 1993, abandoned, which is a continuation-in-part of Ser. No. 771,262, Oct. 4, 1991, and a continuation-in-part of Ser. No. 532,254, Jun. 1, 1990, Pat. No. 5,177,193, which is a continuation-in-part of Ser. No. 313,646, Feb. 21, 1989, abandoned.

[51] Int. Cl.$^6$ .................... A61K 38/24; C07K 14/59
[52] U.S. Cl. .................. 514/8; 530/397; 530/398; 530/399; 514/2
[58] Field of Search .............. 514/2, 8; 435/69.4, 435/69.7, 172.3; 530/397, 398, 399

[56] References Cited

U.S. PATENT DOCUMENTS

| 4,717,670 | 1/1988 | Beck ............................. 435/69.4 |
| 4,935,233 | 6/1990 | Bell et al. ....................... 424/85.5 |
| 5,177,193 | 1/1993 | Boime et al. ..................... 530/397 |
| 5,264,558 | 11/1993 | Kim ............................. 530/402 |
| 5,338,835 | 8/1994 | Boime ........................... 530/398 |
| 5,420,247 | 5/1995 | Gearing et al. .................. 530/350 |

FOREIGN PATENT DOCUMENTS

| 0 163 406 | 12/1985 | European Pat. Off. . |
| 01959 | 5/1985 | WIPO . |
| WO91/16922 | 11/1991 | WIPO . |

OTHER PUBLICATIONS

"Polyclonal antibodies against the polypeptide and carbohydrate epitopes of recombinant human choriogonadotropin β–subunit," *Molecular and Cellular Endocrinology*, Vol. 86, issued 1992, W. Chen et al.

"Protein engineering of antibody binding sites: Recovery of specific activity in an anti–digoxin single–chain Fv analogue produced in *Escherichia coli*," *Proc. Nat. Acad. Sci. USA*, Vol. 85, issued Aug. 1988, J.S. Huston et al.

LaPolt, P.S. et al.; Enhanced Stimulation of Follicle Maturation and Ovulatory Potential by Long Acting Follicle––Stimulating Agonists wtih Extended Carboxyl–Terminal Peptides; *Endocrinology* (1992) *131*:2514–2520.

Fares, F.A. et al.; Design of a Long–acting Follitropin Agonist by Fusing the C–terminal Sequence of the Chorionic Gonadatropin β Subunit to the Follitropin β Subunit; *Proc Natl Acad Sci USA* (1992) 89:4304–4308.

Lapthorn, A.J. et al.; Crystal Structure of Human Chorionic Gonadatropin; *Nature* (1994) *369*:455–461.

Wu, H. et al.; Structure of Human Chorionic Gonadotropin at 2.6 Å Resolution from MAD Analysis of the Selenomethionyl Protein; *Structure* (1994) 2:545–558.

Patel, D.J.; A Clasped Embrace; *Nature* (1994) *369*:438–439.

*Primary Examiner*—Stephen Walsh
*Assistant Examiner*—Lorraine Spector
*Attorney, Agent, or Firm*—Morrison & Foerster LLP

[57] ABSTRACT

Single-chain forms of the glycoprotein hormone quartet, at least some members of which are found in most vertebrates, are disclosed. The single chain compounds of the invention comprise two β subunits of the glycoprotein hormones, which β subunits are the same or different. These "two-β" forms are antagonists of glycoprotein hormone activity.

11 Claims, 4 Drawing Sheets

COVALENTLY LINKED β SUBUNITS OF THE GLYCOPROTEIN HORMONES AS ANTAGONISTS

CROSS-REFERENCE TO RELATED APPLICATIONS

This application is a continuation-in-part of U.S. Ser. No. 08/310,590 filed 22 Sep. 1994 which is a continuation-in-part of U.S. Ser. No. 08/289,396 filed 12 Aug. 1994 which is a continuation-in-part of U.S. Ser. No. 08/049,869 filed 20 Apr. 1993 now abandoned, which is a continuation-in-part of U.S. application Ser. No. 07/771,262 filed 4 Oct. 1991; it is also a continuation-in-part of U.S. Ser. No. 07/532,254 filed 1 Jun. 1990, now U.S. Pat. No. 5,177,193 which is a continuation-in-part of U.S. application Ser. No. 07/313,646 filed 21 Feb. 1989 and now abandoned. The disclosures of the above-mentioned applications are incorporated herein by reference.

ACKNOWLEDGEMENT OF GOVERNMENT SUPPORT

This invention was made with government support under NIH Contract No. NO1-HD-9-2922, awarded by the National Institutes of Health. The government has certain rights in this invention.

TECHNICAL FIELD

The invention relates to the field of protein engineering and the glycoprotein hormones which occur normally as heterodimers. More specifically, the invention concerns single-chain forms of chorionic gonadotropin (CG), thyroid stimulating hormone (TSH), luteinizing hormone (LH), and follicle stimulating hormone (FSH).

BACKGROUND ART

In humans, four important glycoprotein hormone heterodimers (LH, FSH, TSH AND CG) have identical α subunits and differing β subunits. Three of these hormones are present in virtually all other vertebrate species as well; CG has so far been found only in primates and in horse placenta and urine.

PCT application WO90/09800, published 7 Sep. 1990, describes a number of modified forms of these hormones. One important modification is C-terminal extension of the β subunit by the carboxy terminal peptide of human chorionic gonadotropin or a variant thereof. Other muteins of these hormones are also described. In addition, U.S. Ser. No. 08/049,869 filed 20 Apr. 1993, the parent application herein, describes modifying these hormones by extension or insertion of the CTP at locations other than the C-terminus. The relevant positions for the CTP are from any one of positions 112–118 to position 145 of the β subunit of human chorionic gonadotropin. The PCT application describes variants of the CTP extension obtained by conservative amino acid substitutions such that the capacity of the CTP to alter the clearance characteristics is not destroyed. The parent application additionally discloses fragments shorter than the sequence extending from positions 112–118 to 145.

The CTP-extended β subunit of FSH is also described in two papers by applicants herein: LaPolt, P. S. et al.; *Endocrinology* (1992) 131:2514–2520 and Fares, F. A. et al.; *Proc Natl Acad Sci USA* (1992) 89:4304–4308. Both of these papers are incorporated herein by reference.

The crystal structure of the heterodimeric form of human chorionic gonadotropin has now been published in more or less contemporaneous articles; one by Lapthorn, A. J. et al. *Nature* (1994) 369:455–461 and the other by Wu, H. et al. *Structure* (1994) 2:545–558. The results of these articles are summarized by Patel, D. J. *Nature* (1994) 369:438–439.

At least one instance of preparing a successful single-chain form of a heterodimer is now known. The naturally occurring sweetener protein, monellin, is isolated from serendipity berries in a heterodimeric form. Studies on the crystal structure of the heterodimer were consistent with the proposition that the C-terminus of the B chain could be linked to the N-terminus of the A chain through a linker which preserved the spatial characteristics of the heterodimeric form. Such a linkage is advantageous because, for use as a sweetener protein, it would be advantageous to provide this molecule in a form stable at high temperatures. This was successfully achieved by preparing the single-chain form, thus impeding heat denaturation, as described in U.S. Pat. No. 5,264,558.

Published PCT application WO91/16922 published 14 Nov. 1991 describes a multiplicity of chimeric and otherwise modified forms of the heterodimeric glycoprotein hormones. In general, the disclosure is focused on chimeras of α subunits or β subunits involving portions of various α or β chains respectively. One construct simply listed in this application, and not otherwise described, fuses substantially all of the β chain of human chorionic gonadotropin to the α subunit preprotein, i.e., including the secretory signal sequence for this subunit. This construct falls outside the scope of the present invention since the presence of the signal sequence intervening between the β and α chains fails to serve as a linker moiety as defined and described herein.

It has now been found that the normally heterodimeric glycoprotein hormones retain their properties when in single-chain form, including single-chain forms that contain the various CTP extensions and insertions described above.

DISCLOSURE OF THE INVENTION

The invention provides single-chain forms of the glycoprotein hormones, at least some of which hormones are found in most vertebrate species. The single-chain forms of the invention may either be glycosylated, partially glycosylated, or nonglycosylated and the α and β chains that occur in the native glycoprotein hormones may be linked through a linker moiety. Particularly preferred linker moieties include the carboxy terminal peptide (CTP) unit either as a complete unit or only as a portion thereof. The resulting single-chain hormones either retain the activity of the unmodified heterodimeric form or are antagonists of this activity.

Thus, in one aspect, the invention is directed to a glycosylated or nonglycosylated protein which comprises the amino acid sequence of the α subunit common to the glycoprotein hormones linked covalently, optionally through a linker moiety, to the amino acid sequence of the β subunit of one of said hormones, or variants of said amino acid sequences wherein said variants are defined herein.

In another aspect, the invention is directed to a glycosylated or nonglycosylated protein which comprises the amino acid sequence of the β subunit of a member of the glycoprotein hormone quartet linked covalently, optionally through a linker moiety, to the amino acid sequence of the β subunit of one of said hormones, or variants of said amino acid sequences wherein said variants are defined herein.

In still another aspect, the invention is directed to glycosylated or nonglycosylated single-chain forms of the biologically important dimers whose efficacy is presaged by the single-chain forms of the hormone quartet. Thus, the invention is also directed to the single-chain forms of interleukins 3 and 12 (IL-3 and IL-12), tumor necrosis factor (TNF), transforming growth factor (TGF) as well as inhibin. Also included are hybrid interleukins such as single chain forms of one subunit from IL-3 and the other from IL-12.

In other aspects, the invention is directed to recombinant materials and methods to produce the single-chain proteins of the invention, to pharmaceutical compositions containing them; to antibodies specific for them; and to methods for their use.

MODES OF CARRYING OUT THE INVENTION

Figure 1:
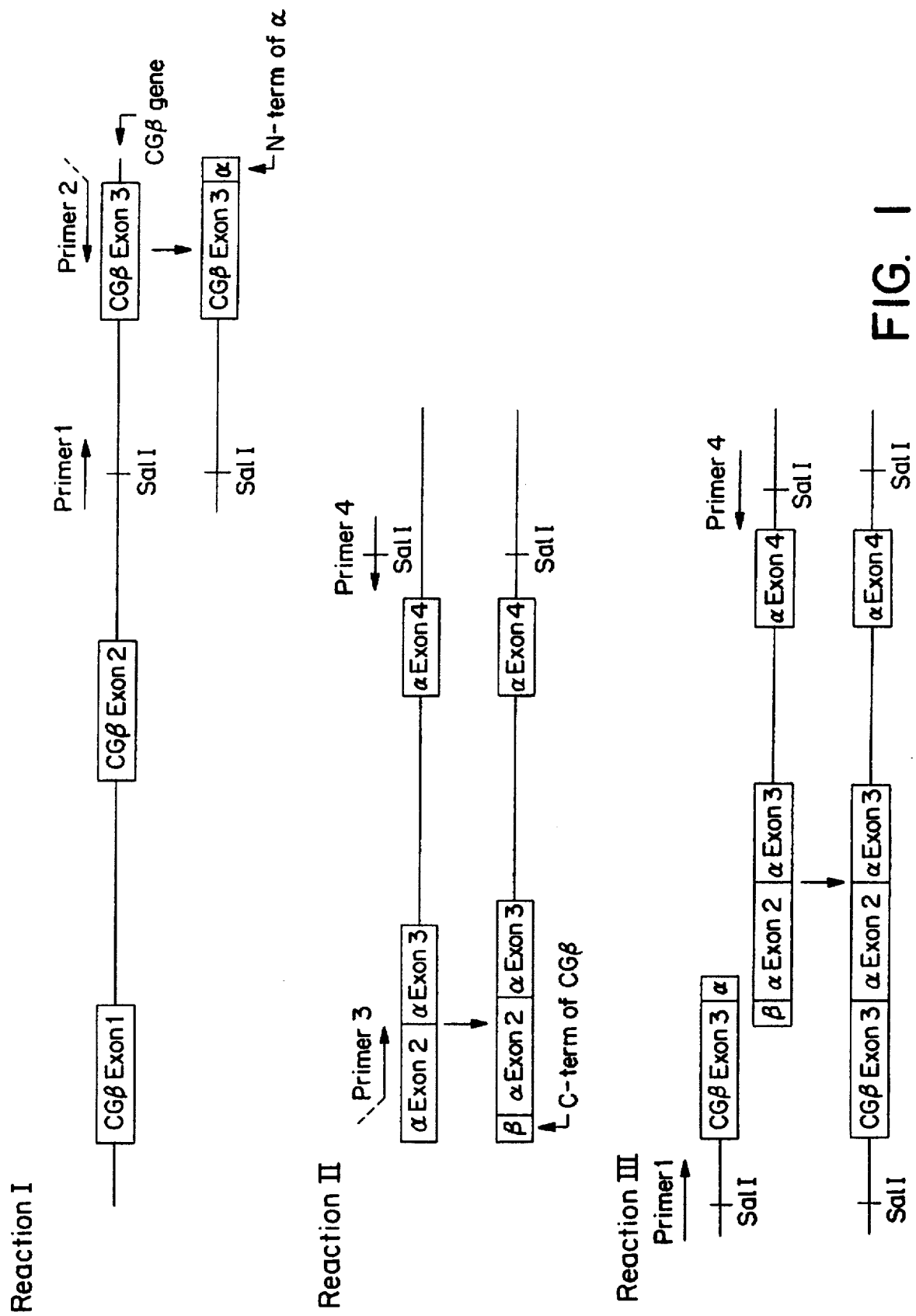
FIG. 1 shows the construction of a SalI bounded DNA fragment fusing the third exon of CGβ with the second exon encoding the α subunit.

Four "glycoprotein" hormones in humans provide a family which includes human chorionic gonadotropin (hCG), follicle stimulating hormone (FSH), luteinizing hormone (LH), and thyroid stimulating hormone (TSH). As used herein, "glycoprotein hormones" refers to the members of this family. All of these hormones are heterodimers comprised of α subunits which, for a given species, are identical in amino acid sequence among the group, and β subunits which differ according to the member of the family. Thus, normally these glycoprotein hormones occur as heterodimers composed of α and β subunits associated with each other but not covalently linked. Most vertebrates produce FSH, TSH and LH; chorionic gonadotropin has been found only in primates, including humans, and horses.

Thus, this hormone "quartet" is composed of heterodimers wherein the α and β subunits of each are encoded in different genes and are separately synthesized by the host. The host then assembles the separately synthesized subunits into a non-covalently linked heterodimeric complex. In this manner, the heterodimers of this hormone quartet differ from heterodimers such as insulin which is synthesized from a single gene (in this case with an intervening "pro" sequence) and the subunits are covalently coupled using disulfide linkages. This hormone quartet is also distinct from the immunoglobulins which are assembled from different loci, but are covalently bound through disulfide linkages. On the other hand, monellin, which is, however, a plant protein, is held together through noncovalent interaction between its A and B chains. It is not known at present whether the two chains are encoded on separate genes.

Thus, a variety of factors is influential in determining the behavior of biologically active compounds which are dimers formed from subunits that are identical or different. The subunits may be covalently or noncovalently linked; they may be synthesized by the same or different genes; and they may or may not contain, in their precursor forms, a "pro" sequence linking the two members of the dimer. Based on the results obtained with the single-chain forms of the glycoprotein hormone quartet herein, it is apparent that single-chain forms of the biologically active dimers interleukin-12, interleukin-3 (IL-12 and IL-3), inhibin, tumor necrosis factor (TNF), and transforming growth factor (TGF) will also be biologically active.

The single-chain forms of the heterodimers or homodimers have a number of advantages over their dimeric forms. First, they are generally more stable. LH, in particular, is noted for its instability and short half-life. Second, problems of recombinant production are reduced since only a single gene need be transcribed, translated and processed. This is particularly important for expression in bacteria. Third, of course, they provide an alternate form thus permitting fine tuning of activity levels and of in vivo half lives. Finally, single chain forms are unique starting materials for identifying truncated forms with the activity of the dimer.

Features of the Members of the Quartet

The β subunit of hCG is substantially larger than the other β subunits in that it contains approximately 34 additional amino acids at the C-terminus referred to herein as the carboxy terminal portion (CTP) which, when glycosylated at the O-linked sites, is considered responsible for the comparatively longer serum half-life of hCG as compared to other gonadotropins (Matzuk, M. et al., Endocrinol (1989) 126:376). In the native hormone, this CTP extension contains four mucin-like O-linked oligosaccharides.

In one embodiment of the present invention, the α and β chains of the glycoprotein hormones are coupled into a single-chain proteinaceous material where the α and β chain are covalently linked, optionally through a linker moiety. The linker moiety may include further amino acid sequence, and in particular the CTP units described herein can be advantageously included in the linker. In addition, the linker may include peptide or nonpeptide drugs which can be targeted to the receptors for the hormones.

Use of a linker moiety would make possible the linkage of the α and β chains in a head-to-head or tail-to-tail configuration in addition to the head-to-tail configuration that is achievable by simply coupling the two peptide chains through a peptide bond. Thus, possible embodiments of the invention include, with the N-terminus at the left, α-FSHβ, βFSH-α, α-BLH, α-CTP-βLH, CTP-βLH-α, CTP-βLH-CTP-α; and the like.

The single chain forms of the heterodimeric gonadotropins or glycoprotein quartet also relate to an additional important set of embodiments wherein rather than coupling the α and β subunits, two β subunits may be coupled together to form a single-chain compound. The coupling can be head to head, head to tail, or tail to tail; head to head and tail to tail couplings involve synthetic chemistry using standard techniques to link two carboxyl or two amino groups through a linker moiety. For example, two amino groups may be linked through an anhydride or through any dicarboxylic acid derivative; two carboxyl groups can be linked through diamines or diols using standard activation techniques. However, the most preferred form is a head to tail configuration wherein standard peptide linkages suffice and the single-chain compound can be prepared as a fusion protein recombinantly or using synthetic peptide techniques either in a single chain or, preferably, ligating individual portions of the entire sequence. Of course, if desired, linker moieties can be used in this case as well, but this is unnecessary and the convenience of recombinant production of the single-chain protein would suggest that this is by far the most preferred approach.

When a head-to-tail configuration is employed, linkers may consist essentially of additional peptide sequence. As is the case with the heterodimers, the two β chains may be linked through a CTP unit as further described below.

The "two-β" single-chain tandem peptides are especially useful as antagonists for the receptors normally activated by the heterodimeric glycoprotein hormones. Since the α subunit is believed largely responsible for signal transduction, while β subunit confers receptor specificity, and since the α and β subunits have similar conformations, the single-chain compounds should be able specifically to bind a receptor for which at least one β chain is present without activating the receptor.

The antagonist activity of the "2-β" single-chain tandem peptides is based in part on the crystal structure of the heterodimers. It is noted that the α and β chains have similar cystine-knot configurations and that some of the folding patterns of the two chains are analogous.

The "two-β" single-chain compounds of the invention may be designed to contain tandem copies of the same β subunit—i.e., FSHβ-FSHβ; HCGβ-HCGβ; TSHβ-TSHβ; or LHβ-LHβ; or chimeric single-chain compounds may be employed such as HCGβ-FSHβ; FSHβ-LHβ; LHβ-TSHβ and the like. There are a total of 12 such possible combinations. In addition, the carboxyl terminal peptide (CTP) of the HCG β subunit improves the conformation of the single-chain compound when present between the two β chains. This is automatic when HCG β is the upstream portion; however in other instances, it is convenient to employ a CTP subunit as described herein at the carboxyl terminus of the upstream participant. Two such CTP units are also included within the invention scope. Thus, preferred embodiments include FSHβ-CTP-FSHβ; FSHβ-CTP-CTP-FSHβ; LHβ-CTP-FSHβ; LHβ-CTP-CTP-FSHβ and the like.

The following definitions may be helpful in describing the single-chain forms of the molecules.

As used herein, α subunit, and FSH, LH, TSH, and CG β subunits as well as the heterodimeric forms have in general their conventional definitions and refer to the proteins having the amino acid sequences known in the art per se, or allelic variants thereof, regardless of the glycosylation pattern exhibited.

"Native" forms of these peptides are those which have the amino acid sequences isolated from the relevant vertebrate tissue, and have these known sequences per se, or their allelic variants.

"Variant" forms of these proteins are those which have deliberate alterations in amino acid sequence of the native protein produced by, for example, site-specific mutagenesis or by other recombinant manipulations, or which are prepared synthetically.

These alterations consist of 1–10, preferably 1–8, and more preferably 1–5 amino acid substitutions, most preferably conservative amino acid substitutions as defined below. The resulting variants must retain activity which affects the corresponding activity of the native hormone—i.e., either they must retain the biological activity of the native hormone directly, or they must behave as antagonists, generally by virtue of being able to bind the receptors for the native hormones but lacking the ability to effect signal transduction. For example, it is known that if the glycosylation site at position 52 of the α subunit is removed by an amino acid substitution, therefore preventing all glycosylation at that site, the hormones which are heterodimers with this altered α subunit are generally agonists and are able to bind receptors preventing the native hormone from doing so in competition. (On the other hand, the glycosylation site of the α subunit at position 78 appears not greatly to affect the activity of the hormones.) Other alterations in the amino acid sequence may also result in antagonist rather than agonist activity for the variant.

Particularly preferred variants are those wherein the glycosylation sites of either the α or β subunits or both have been altered. The α subunit contains two glycosylation sites, one at position 52 and the other at position 78, and the effect of alterations of these sites on activity has just been described. Similarly, the β subunits generally contain two N-linked glycosylation sites (at positions that vary somewhat with the nature of the β chain) and similar alterations can be made at these sites. The CTP extension of hCG contains four O-linked glycosylation sites, and conservative mutations at the serine residues (e.g., conversion of the serine to alanine) destroys these sites. Destruction of the O-linked glycosylation sites may effect conversion of against activity to antagonist activity.

Finally, alterations in amino acid sequence that are proximal to the N-linked or O-linked glycosylation sites influence the nature of the glycosylation that is present on the resulting molecule and also alter activity.

Alterations in amino acid sequence include both substitutions and deletions. Thus, truncated forms of the hormones are included among variants, e.g., mutants of the α subunit which are lacking some or all of the amino acids at positions 85–92 at the C-terminus. In addition, α subunits with 1–10 amino acids deleted from the N-terminus are included. Some useful variants of the hormone quartet described herein are set forth in U.S. Pat. No. 5,177,193 issued 5 Jan. 1993 and incorporated herein by reference. As shown therein, the glycosylation patterns can be altered by destroying the relevant sites or, in the alternative, by choice of host cell in which the protein is produced.

There is considerable literature on variants of the hormone quartet described herein and it is clear from this literature that a large number of possible variants which result both in agonist and antagonist activity can be prepared. Such variants are disclosed, for example, in Chen, F. et al. *Molec Endocrinol* (1992) 6:914–919; Yoo, J. et al. *J Biol Chem* (1993) 268:13034–13042; Yoo, J. et al. *J Biol Chem* (1991) 266:17741–17743; and Bielinska, M. et al. *J Cell Biol* (1990) 111:330a (Abstract 1844).

As described hereinabove, one method of constructing effective antagonists is to prepare a single-chain molecule containing two β subunits of the same or different member of the glycoprotein quartet. Particularly preferred variants of these single-chain forms include those wherein one or more cystine-link is deleted, typically by substituting a neutral amino acid for one or both cysteines which participate in the link. Particularly preferred cystine links which may be deleted are those between positions 26 and 110 and between positions 23 and 72.

In addition, it has been demonstrated that the β subunits of the hormone quartet can be constructed in chimeric forms so as to provide biological functions of both components of the chimera, or, in general, hormones of altered biological function. Thus, chimeric molecules which exhibit both FSH and LH/CG activities can be constructed as described by Moyle, *Proc Natl Acad Sci* (1991) 88:760–764; Moyle, *Nature* (1994) 368:251–255. As disclosed in these papers, substituting amino acids 101–109 of FSH-β for the corresponding residues in the CG-β subunit yields an analog with both hCG and FSH activity.

These chimeric forms of β subunits can also be used in the single-chain compounds which couple to β subunits into a single molecule.

Although it is recognized that glycosylation pattern has a profound influence on activity both qualitatively and quantitatively, for convenience the terms FSH, LH, TSH, and CG β subunits refers to the amino acid sequence characteristic of the peptides, as does "α subunit." When only the β chain is referred to, the terms will be, for example, FSH β; when the heterodimer is referred to, the simple term "FSH" will be used. It will be clear from the context in what manner the glycosylation pattern is affected by, for example, recombinant expression host or alteration in the glycosylation sites. Forms of the glycoprotein with specified glycosylation patterns will be so noted.

As used herein "peptide" and "protein" are used interchangeably, since the length distinction between them is arbitrary.

In the single-chain forms of the present invention, the α and/or β chain my contain a CTP extension inserted into a noncritical region.

"Noncritical" regions of the α and β subunits are those regions of the molecules not required for biological activity (including agonist and antagonist activity). In general, these regions are removed from binding sites, precursor cleavage sites, and catalytic regions. Regions critical for inducing proper folding, binding to receptors, catalytic activity and the like should be avoided; similarly, regions which are critical to assure the three-dimensional conformation of the protein should be avoided. The ascertainment of noncritical regions is readily accomplished by deleting or modifying candidate regions and conducting an appropriate assay for the desired activity. Regions where modifications result in loss of activity are critical; regions wherein the alteration results in the same or similar activity are considered noncritical.

It should be emphasized, that by "biological activity" is meant activity which is either agonistic or antagonistic to that of the native hormones. Thus, certain regions are critical for behavior of a variant as an antagonist, even though the antagonist is unable to directly provide the physiological effect of the hormone.

For example, for the α subunit, positions 33–59 are thought to be necessary for signal transduction and the 20 amino acid stretch at the carboxy terminus is needed for signal transduction/receptor binding. Residues critical for assembly with the β subunit include at least residues 33–58, particularly 37–40.

Where the noncritical region is "proximal" to the N- or C-terminus, the insertion is at any location within 10 amino acids of the terminus, preferably within 5 amino acids, and most preferably at the terminus per se.

In general, "proximal" is used to indicate a position which is within 10 amino acids, preferably within five amino acids, of a referent position, and most preferably at the referent position per se. Thus, certain variants may contain substitutions of amino acids "proximal" to a glycosylation site; the definition is relevant here. In addition, the α and β subunits may be linked to each other at positions "proximal" to their N- or C-termini.

Figure 2:
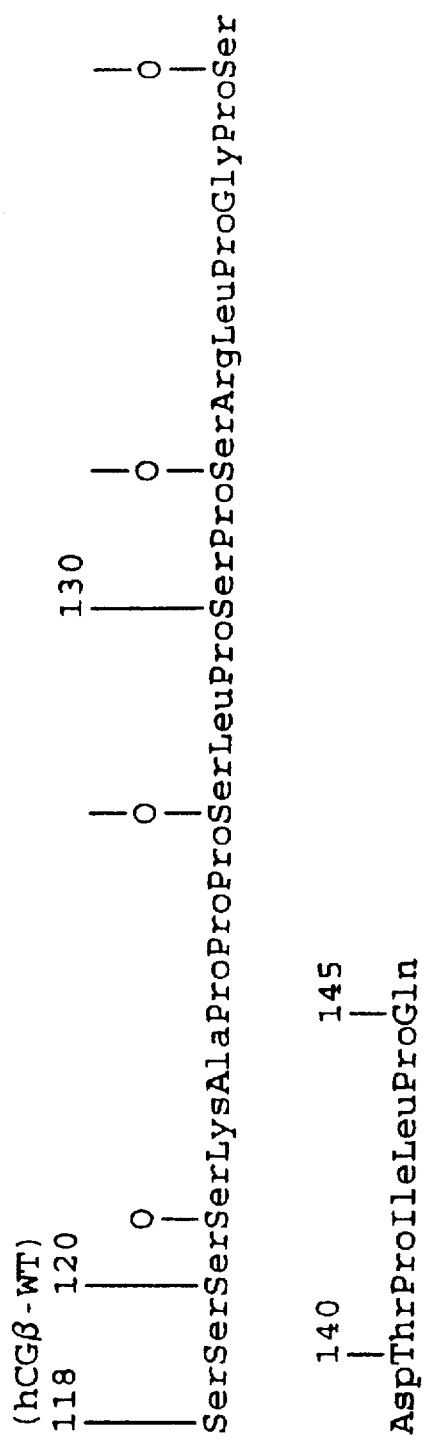
FIG. 2 shows the amino acid sequence and numbering of positions 112–145 of human CGβ.

As used herein, the "CTP unit" refers to an amino acid sequence found at the carboxy terminus of human chorionic gonadotropin β subunit which extends from amino acid 112–118 to residue 145 at the C-terminus or to a portion thereof. Thus, each "complete" CTP unit contains 28–34 amino acids, depending on the N-terminus of the CTP. The native sequence of positions 112–145 is shown in FIG. 2.

By a "partial" CTP unit is meant an amino acid sequence which occurs between positions 112–118 to 145 inclusive, but which has at least one amino acid deleted from the shortest possible "complete" CTP unit (i.e. from positions 118–145). The "partial" CTP units included in the invention preferably contain at least one O-glycosylation site if agonist activity is desired. Some nonglycosylated forms of the hormones are antagonists and are useful as such. The CTP unit contains four such sites at the serine residues at positions 121 (site 1); 127 (site 2); 132 (site 3); and 138 (site 4). The partial forms of CTP useful in agonists of the invention will contain one or more of these sites arranged in the order in which they appear in the native CTP sequence. Thus, the "partial" CTP unit employed in agonists of the invention may include all four glycosylation sites; sites 1, 2 and 3; sites 1, 2 and 4; sites 1, 3 and 4; sites 2, 3 and 4; or simply sites 1 and 2; 1 and 3; 1 and 4; 2 and 3; 2 and 4; or 3 and 4; or may contain only one of sites 1, 2, 3 or 4.

By "tandem" inserts or extensions is meant that the insert or extension contains at least two "CTP units" Each CTP unit may be complete or a fragment, and native or a variant. All of the CTP units in the tandem extension or insert may be identical, or they may be different from each other. Thus, for example, the tandem extension or insert may generically be partial-complete; partial-partial; partial-complete-partial; complete-complete-partial, and the like wherein each of the noted partial or complete CTP units may independently be either a variant or the native sequence.

The "linker moiety" is a moiety that joins the α and β sequences without interfering with the activity that would otherwise be exhibited by the same α and β chains as members of a heterodimer, or which alters that activity to convert it from agonist to antagonist activity. The level of activity may change within a reasonable range, but the presence of the linker cannot be such so as to deprive the single-chain form of both substantial agonist and substantial antagonist activity. The single-chain form must remain as a single-chain form when it is recovered from its production medium and must exhibit activity pertinent to the hormonal activity of the heterodimer, the elements of which form its components.

Variants

The hormone subunits and the CTP units may correspond exactly to the native hormone or CTP sequence, or may be variants. The nature of the variants has been defined hereinabove. In such variants, 1–10, preferably 1–8, and most preferably 1–5 of the amino acids contained in the native sequence are substituted by a different amino acid compared to the native amino acid at that position, or 1–10, more preferably 1–8 and most preferably 1–5 amino acids are simply deleted or combination of these. The substitutions or deletions taken cumulatively do not result in substantial elimination of agonist or antagonist activity associated with the hormone. Substitutions by conservative analogs of the native amino acid are preferred.

"Conservative analog" means, in the conventional sense, an analog wherein the residue substituted is of the same general amino acid category as that for which substitution is made. Amino acids have been classified into such groups, as is understood in the art, by, for example, Dayhoff, M. et al., *Atlas of Protein Sequences and Structure* (1972) 5:89–99. In general, acidic amino acids fall into one group; basic amino acids into another; neutral hydrophilic amino acids into another; and so forth.

More specifically, amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

no acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows.

Acidic: Aspartic acid and Glutamic acid;
Basic/noncyclic: Arginine, Lysine;
Basic/cyclic: Histidine;
Neutral/polar/small: Glycine, serine, cysteine;
Neutral/nonpolar/small: Alanine;
Neutral/polar/large/nonaromatic: Threonine, Asparagine, Glutamine;
Neutral/polar/large aromatic: Tyrosine;
Neutral/nonpolar/large/nonaromatic: Valine, Isoleucine, Leucine, Methionine;
Neutral/nonpolar/large/aromatic: Phenylalanine, and Tryptophan.

The gene-encoded secondary amino acid proline, although technically within the group neutral/nonpolar/large/cyclic and nonaromatic, is a special case due to its known effects on the secondary conformation of peptide chains, and is not, therefore, included in this defined group.

If the single-chain proteins of the invention are constructed by recombinant methods, they will contain only gene encoded amino acid substitutions; however, if any portion is synthesized by standard, for example, solid phase, peptide synthesis methods and ligated, for example, enzymatically, into the remaining protein, non-gene encoded amino acids, such as aminoisobutyric acid (Aib), phenylglycine (Phg), and the like can also be substituted for their analogous counterparts.

These non-encoded amino acids also include, for example, β-alanine (β-Ala), or other omega-amino acids, such as 3-amino propionic, 4-amino butyric and so forth, sarcosine (Sar), ornithine (Orn), citrulline (Cit), t-butylalanine (t-BuA), t-butylglycine (t-BuG), N-methylisoleucine (N-MeIle), and cyclohexylalanine (Cha), norleucine (Nle), cysteic acid (Cya) 2-naphthylalanine (2-Nal); 1,2,3,4-tetrahydroisoquinoline-3-carboxylic acid (Tic); mercaptovaleric acid (Mvl); β-2-thienylalanine (Thi); and methionine sulfoxide (MSO). These also fall conveniently into particular categories.

Based on the above definitions,

Sar and β-Ala and Aib are neutral/nonpolar/small;
t-BuA, t-BuG, N-MeIle, Nle, Mvl and Cha are neutral/nonpolar/large/nonaromatic;
Orn is basic/noncyclic;
Cya is acidic;
Cit, Acetyl Lys, and MSO are neutral/polar/large/nonaromatic; and
Phg, Nal, Thi and Tic are neutral/nonpolar/large/aromatic.

The various omega-amino acids are classified according to size as neutral/nonpolar/small (β-Ala, i.e., 3-aminopropionic, 4-aminobutyric) or large (all others).

Thus, amino acid substitutions other than those encoded in the gene can also be included in peptide compounds within the scope of the invention and can be classified within this general scheme according to their structure.

Preferred Embodiments of the Single-Chain Hormones

The single-chain hormones of the invention are most efficiently and economically produced using recombinant techniques. Therefore, those forms of α and β chains, CTP units and other linker moieties which include only gene-encoded amino acids are preferred. It is possible, however, as set forth above, to construct at least portions of the single-chain hormones using synthetic peptide techniques or other organic synthesis techniques and therefore variants which contain nongene-encoded amino acids are also within the scope of the invention.

In the most preferred embodiments of the single-chain hormones of the invention, the C-terminus of the β subunit is covalently linked, optionally through a linker, to the N-terminus of the mature α subunit; forms wherein the C-terminus of the α subunit is linked to the N-terminus of the β subunit are also useful, but often have less activity either as antagonists or agonists of the relevant receptor. The linkage can be a direct peptide linkage wherein the C-terminal amino acid of one subunit is directly linked through the peptide bond to the N-terminus of the other; however, in many instances it is preferable to include a linker moiety between the two termini. In many instances, the linker moiety will provide at least one β turn between the two chains. The presence of proline residues in the linker may therefore be advantageous.

As described above, the N-terminus of the α chain may also be coupled to the N-terminus of the β chain or the C-terminus of the α to the C-terminus of the β chain in any case through a linker unit.

Preferred embodiments of the single-chain compounds containing two β subunits are those wherein the C-terminus of one unit is linked to the N-terminus of the other, optionally through a linker, preferably a peptide linker. Also possible, as described above, are linkages between the N-termini of the two β chains or linkages between the C-termini of the two β chains; in these cases, of course, a linker is required.

While the head-to-head, tail-to-tail and head-to-tail configurations of both the single-chain heterodimer and the single-chain two-β subunit form have been described, the linkage between the two subunits may also occur at positions not precisely at the N- or C-terminus of each member but at positions proximal thereto.

In one particularly preferred set of embodiments, the linkage is head-to-tail and the linker moiety will include one or more CTP units and/or variants or truncated forms thereof. Preferred forms of the CTP units used in such linker moieties are described hereinbelow.

Further, the linker moiety may include a drug covalently, preferably releasably, bound to the linker moiety. Means for coupling the drug to the linker moiety and for providing for its release are conventional.

In addition to their occurrence in the linker moiety, CTP and its variants and truncations may also be included in any noncritical region of the subunits making up the single-chain hormone. The nature of these inclusions, and their positions, is set forth in detail in the parent application herein.

While CTP units are preferred inclusions in the linker moiety, it is understood that the linker may be any suitable covalently bound material which provides the appropriate spatial relationship between the α and β subunits. Thus, for head-to-tail configurations the linker may generally be a peptide comprising an arbitrary number, but typically less than 100, more preferably less than 50 amino acids which has the proper hydrophilicity/hydrophobicity ratio to provide the appropriate spacing and confirmation in solution. In general, the linker should be on balance hydrophilic so as to reside in the surrounding solution and out of the way of the interaction between the α and β subunits or the two β subunits. It is preferable that the linker include β turns typically provided by proline residues. Any suitable polymer, including peptide linkers, with the above-described correct characteristics may be used.

One particular linker moiety that is not included within the scope of the invention is that which includes a signal peptide immediately upstream of the downstream subunit.

Particularly preferred embodiments of the single-chain hormones of the invention include:

βFSH-α; βFSH-βFSH; βFSH-βLH; βLH-α; βLH-βLH; βLH-βFSH; βTSH-α; βTSH-βTSH; βTSH-βFSH; βCG-α; β-CG-β-CG; βCG-βFSH; βCG-βTSH; βFSH-CTP-α; βFSH-CTP-βFSH; βFSH-CTP-βLH; βLH-CTP-α; βLH-CTP-βLH; βLH-CTP-βFSH; βCG-CTP-α; βFSH-CTP-CTP-βLH; βFSH-CTP-CTP-α; βFSH-CTP-CTP-βTSH; βLH-CTP-CTP-α; βLH-CTP-CTP-βLH; βCG-CTP-CTP-α; βCG-CTP-CTP-βLH;

and the like. Also particularly preferred are the human forms of the subunits. In the above constructions, "CTP" refers to CTP or its variants or truncations as further explained in the paragraph below.

Preferred Embodiments of CTP Units

The notation used for the CTP units of the invention is as follows: for portions of the complete CTP unit, the positions included in the portion are designated by their number as they appear in FIG. 2 herein. Where substitutions occur, the substituted amino acid is provided along with a superscript indicating its position. Thus, for example, CTP (120–143) represents that portion of CTP extending from positions 120 to 143; CTP (120–130; 136–143) represents a fused amino acid sequence lacking positions 118–119, 131–135, and 144–145 of the native sequence. CTP (Arg$^{122}$) refers to a variant wherein the lysine at position 122 is substituted by an arginine; CTP (Ile$^{134}$) refers to a variant wherein the leucine at position 134 is substituted by isoleucine. CTP (Val$^{128}$Val$^{143}$) represents a variant wherein two substitutions have been made, one for the leucine at position 128 and the other for the isoleucine at position 142. CTP (120–143; Ile$^{128}$ Ala$^{130}$) represents the relevant portion of the CTP unit where the two indicated substitutions have been made.

Also preferred among variants of CTP are those wherein one or more of the O-linked glycosylation sites have been altered or deleted. One particularly preferred means of altering the site to prevent glycosylation is substitution of an alanine residue for the serine residue in these sites.

Particularly preferred are those CTP units of the following formulas:

1 CTP (116–132)
2 CTP (118–128; 130–135)
3 CTP (117–142)
4 CTP (116–130)
5 CTP (116–123; 137–145)
6 CTP (115–133; 141–145)
7 CTP (117–140, Ser$^{123}$ Gln$^{140}$)
8 CTP (125–143, Ala$^{130}$)
9 CTP (135–145, Glu$^{139}$)
10 CTP (131–143, Val$^{142}$ Val$^{143}$)
11 CTP (118–132)
12 CTP (118–127)
13 CTP (118–145)
14 CTP (115–132)
15 CTP (115–127)
16 CTP (115–145)
17 CTP (112–145)
18 CTP (112–132)
19 CTP (112–127)

Preferred Embodiments of the α and β Subunits

Of course, the native forms of the α and β subunits in the single-chain form are among the preferred embodiments. However, certain variants are also preferred.

In particular, variants of the α subunit in which the N-linked glycosylation site at position 52 is eliminated or altered by amino acid substitutions at or proximal to this site are preferred for antagonist activity. Similar modifications at the glycosylation site at position 78 are also preferred. Deletion of one or more amino acids at positions 85–92 also affects the nature of the activity of hormones containing the α subunit and substitution or deletion of amino acids at these positions is also among the preferred embodiments.

Similarly, the N-linked glycosylation sites in the β chain can conveniently be modified to eliminate glycosylation and thus affect the agonist or antagonist activity of the β chains. If CTP is present, either natively as in CG or by virtue of being present as a linker, the O-linked glycosylation sites in this moiety may also be altered.

Particular variants containing modified or deleted glycosylation sites are set forth in Yoo, J. et al. *J Biol Chem* (1993) 268:13034–13042; Yoo, J. et al. *J Biol Chem* (1991) 266:17741–17743; and Bielinska, M. et al. *J Cell Biol* (1990) 111:330a (all cited above) and in Matzuk, M. M. et al. *J Biol Chem* (1989) 264:2409–2414; Keene, J. L. et al. *J Biol Chem* (1989) 264:4769–4775; and Keene, J. L. et al. *Mol Endocrinol* (1989) 3:2011–2017.

Not only my the glycosylation sites per se be modified directly, but positions proximal to these sites are preferentially modified so that the glycosylation status of the mutant will be affected. For the α subunit, for example, variants in which amino acids between positions 50–60 are substituted, including both conservative and nonconservative substitutions, are favored, especially substitutions at positions 51, 53 and 55 because of their proximity to the glycosylation site at Also preferred are mutants of the α subunit wherein lysine at position 91 is converted to methionine or glutamic acid.

Suitable Drugs

Suitable drugs that may be included in the linker moiety include peptides or proteins such as insulin-like growth factors; epidermal growth factors; acidic and basic fibroblast growth factors; platelet-derived growth factors; the various colony stimulating factors, such as granulocyte CSF, macrophage-CSF, and the like; as well as the various cytokines such as IL-2, IL-3 and the plethora of additional interleukin proteins; the various interferons; tumor necrosis factor; and the like. Peptide- or protein-based drugs have the advantage that they can be included in the single-chain and the entire construct can readily be produced by recombinant expression of a single gene. Also, small molecule drugs such as antibiotics, antiinflammatories, toxins, and the like can be used.

In general, the drugs included within the linker moiety will be those desired to act in the proximity of the receptors to which the hormones ordinarily bind. Suitable provision for release of the drug from inclusion within the linker will be provided, for example, by also including sites for enzyme-catalyzed lysis as further described under the section headed Preparation Methods hereinbelow.

Other Modifications

The single-chain proteins of the invention may be further conjugated or derivatized in ways generally understood to derivatize amino acid sequences, such as phosphorylation, glycosylation, deglycosylation of ordinarily glycosylated forms, modification of the amino acid side chains (e.g., conversion of proline to hydroxyproline) and similar modifications analogous to those post-translational events which have been found to occur generally.

The glycosylation status of the hormones of the invention is particularly important. The hormones may be prepared in nonglycosylated form either by producing them in procaryotic hosts or by mutating the glycosylation sites normally present in the subunits and/or any CTP units that may be present. Both nonglycosylated versions and partially glycosylated versions of the hormones can be prepared by manipulating the glycosylation sites. Normally, glycosylated versions are, of course, also included within the scope of the invention.

As is generally known in the art, the single-chain proteins of the invention may also be coupled to labels, carriers, solid supports, and the like, depending on the desired application. The labeled forms may be used to track their metabolic fate; suitable labels for this purpose include, especially, radioisotope labels such as iodine 131, technetium 99, indium 111, and the like. The labels may also be used to mediate detection of the single-chain proteins in assay systems; in this instance, radioisotopes may also be used as well as enzyme labels, fluorescent labels, chromogenic labels, and the like. The use of such labels is particularly helpful for these proteins since they are targeting agents receptor ligand.

The proteins of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of bifunctional linkers, can be employed.

Similar linking techniques, along with others, may be employed to couple the proteins of the invention to solid supports. When coupled, these proteins can then be used as affinity reagents for the separation of desired components with which specific reaction is exhibited.

Preparation Methods

Methods to construct the proteins of the invention are well known in the art. As set forth above, if only gene encoded amino acids are included, and the single-chain is in a head-to-tail configuration, the most practical approach at present is to synthesize these materials recombinantly by expression of the DNA encoding the desired protein. DNA containing the nucleotide sequence encoding the single-chain forms, including variants, can be prepared from native sequences. Techniques for site-directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available compatible with a wide variety of hosts, including procaryotic hosts such as bacteria and eucaryotic hosts such as yeast, plant cells, insect cells, mammalian cells, arian cells, and the like.

The choice of host is particularly to posttranslational events, most particularly including glycosylation. The location of glycosylation is mostly controlled by the nature of the glycosylation sites within the molecule; however, the nature of the sugars occupying this site is largely controlled by the nature of the host. Accordingly, a fine-tuning of the properties of the hormones of the invention can be achieved by proper choice of host.

A particularly preferred form of gene for the $\alpha$ subunit portion, whether the $\alpha$ subunit is modified or unmodified, is the "minigene" construction.

As used herein, the $\alpha$ subunit "minigene" refers to the gene construction disclosed in Matzuk, M. M., et al, *Mol Endocrinol* (1988) 2:95–100, in the description of the construction of pM$^2$/CG $\alpha$ or pM$^2$/$\alpha$. This "minigene" is characterized by retention only of the intron sequence between exon 3 and exon 4, all upstream introns having been deleted. In the particular construction described, the N-terminal coding sequences which are derived from exon 2 and a portion of exon 3 are supplied from cDNA and are ligated directly through an XbaI restriction site into the coding sequence of exon 3 so that the introns between exons I and II and between exons II and III are absent. However, the intron between exons III and IV as well as the signals 3' of the coding sequence are retained. The resulting minigene can conveniently be inserted as a BamHI/BglII segment. Other means for construction of a comparable minigene are, of course, possible and the definition is not restricted to the particular construction wherein the coding sequences are ligated through an XbaI site. However, this is a convenient means for the construction of the gene, and there is no particular advantage to other approaches, such as synthetic or partially synthetic preparation of the gene. The definition includes those coding sequences for the $\alpha$ subunit which retain the intron between exons III and IV, or any other intron and preferably no other introns.

For recombinant production, modified host cells using expression systems are used and cultured to produce the desired protein. These terms are used herein as follows:

A "modified" recombinant host cell, i.e., a cell "modified to contain" with the recombinant expression systems of the invention, refers to a host cell which has been altered to contain this expression system by any convenient manner of introducing it, including transfection, viral infection, and so forth. "Modified" refers to cells containing this expression system whether the system is integrated into the chromosome or is extrachromosomal. The "modified" cells may either be stable with respect to inclusion of the expression system or not. In short, "modified" recombinant host cells with the expression system of the invention refers to cells which include this expression system as a result of their manipulation to include it, when they natively do not, regardless of the manner of effecting this incorporation.

"Expression system" refers to a DNA molecule which includes a coding nucleotide sequence to be expressed and those accompanying control sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

If secretion of the protein produced is desired, additional nucleotide sequences encoding a signal peptide are also included so as to produce the signal peptide operably linked to the desired single-chain hormone to produce the preprotein. Upon secretion, the signal peptide is cleaved to release the mature single-chain hormone.

As used herein "cells," "cell cultures," and "cell lines" are used interchangeably without particular attention to nuances of meaning. Where the distinction between them is important, it will be clear from the context. Where any can be meant, all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

All or a portion of the hormones of the invention may be synthesized directly using peptide synthesis techniques known in the art. Synthesized portions may be ligated, and release sites for any drug contained in the linker moiety introduced by standard chemical means. For those embodiments which contain amino acids which are not encoded by the gene and those embodiments wherein the head-to-head or tail-to-tail configuration is employed, of course, the synthesis must be at least partly at the protein level. Head-to-head junctions at the natural N-termini or at positions proximal to the natural N-termini may be effected through linkers which contain functional groups reactive with amino groups, such as dicarboxylic acid derivatives. Tail-to-tail configurations at the C-termini or positions proximal to the C-termini may be effected through linkers which are diamines, diols, or combinations thereof.

Antibodies

The proteins of the invention may be used to generate antibodies specifically immunoreactive with these new compounds. These antibodies are useful in a variety of diagnostic and therapeutic applications.

The antibodies are generally prepared using standard immunization protocols in mammals such as rabbits, mice, sheep or rats, and the antibodies are titered as polyclonal antisera to assure adequate immunization. The polyclonal antisera can then be harvested as such for use in, for example, immunoassays. Antibody-secreting cells from the host, such as spleen cells, or peripheral blood leukocytes, may be immortalized using known techniques and screened for production of monoclonal antibodies immunospecific with the proteins of the invention.

By "immunospecific for the proteins" is meant antibodies which are immunoreactive with the single-chain proteins, but not with the heterodimers per se within the general parameters considered to determine affinity or nonaffinity. It is understood that specificity is a relative term, and an arbitrary limit could be chosen, such as a difference in immunoreactivity of 100-fold or greater. Thus, an immunospecific antibody included within the invention is at least 100 times more reactive with the single-chain protein than with the corresponding heterodimers.

Formulation

The proteins of the invention are formulated and administered using methods comparable to those known for the heterodimers corresponding to the single-chain form. Thus, formulation and administration methods will vary according to the particular hormone used. However, the dosage level and frequency of administration may be altered as compared to the heterodimer, especially if CTP units are present in view of the extended biological half life due to its presence.

Formulations for proteins of the invention are those typical of protein or peptide drugs such as found in Remington's Pharmaceutical Sciences, latest edition, Mack Publishing Company, Easton, Pa. Generally, proteins are administered by injection, typically intravenous, intramuscular, subcutaneous, or intraperitoneal injection, or using formulations for transmucosal or transdermal delivery. These formulations generally include a detergent or penetrant such as bile salts, fusidic acids, and the like. These formulations can be administered as aerosols or suppositories or, in the case of transdermal administration, in the form of skin patches.

Oral administration is also possible provided the formulation protects the peptides of the invention from degradation in the digestive system.

Optimization of dosage regimen and formulation is conducted as a routine matter and as generally performed in the art.

Methods of Use

The single-chain peptides of the invention may be used in many ways, most evidently as substitutes for the heterodimeric forms of the hormones. Thus, like the heterodimers, the agonist forms of the single-chain hormones of the invention can be used in treatment of infertility, as aids in in vitro fertilization techniques, and other therapeutic methods associated with the native hormones.

The single-chain hormones are also useful as reagents in a manner similar to the heterodimers.

In addition, the single-chain hormones of the invention may be used as diagnostic tools to detect the presence or absence of antibodies with respect to the native proteins in biological samples. They are also useful as control reagents in assay kits for assessing the levels of these hormones in various samples. Protocols for assessing levels of the hormones themselves or of antibodies raised against them are standard immunoassay protocols commonly known in the art. Various competitive and direct assay methods can be used involving a variety of labeling techniques including radio-isotope labeling, fluorescence labeling, enzyme labeling and the like.

The single-chain hormones of the invention are also useful in detecting and purifying receptors to which the native hormones bind. Thus, the single-chain hormones of the invention may be coupled to solid supports and used in affinity chromatographic preparation of receptors or antihormone antibodies. The resulting receptors are themselves useful in assessing hormone activity for candidate drugs in screening tests for therapeutic and reagent candidates.

Finally, the antibodies uniquely reactive with the single-chain hormones of the invention can be used as purification tools for isolation of subsequent preparations of these materials. They can also be used to monitor levels of the single-chain hormones administered as drugs.

The following examples are intended to illustrate but not to limit the invention.

EXAMPLE 1

Preparation of DNA Encoding CGβ-α

FIG. 1 shows the construction of an insert for an expression vector wherein the C-terminus of the β-chain of human CG is linked to the N-terminus of the mature human α subunit.

As shown in FIG. 1, the polymerase chain reaction (PCR) is utilized to fuse the two subunits between exon 3 of CGβ and exon 2 of the α subunit so that the codon for the carboxy terminal amino acid of CGβ is fused directly in reading frame to that of the N-terminal amino acid of the α subunit. This is accomplished by using a hybrid primer to amplify a fragment containing exon 3 of CGβ wherein the hybrid primer contains a "tail" encoding the N-terminal sequence of the α subunit. The resulting amplified fragment thus contains a portion of exon 2 encoding human CGα.

Independently, a hybrid primer encoding the N-terminal sequence of the α subunit fused to the codons corresponding to the C-terminus of CGβ is used as one of the primers to amplify the α minigene. The two amplified fragments, each now containing overlapping portions encoding the other subunit are together amplified with two additional primers covering the entire span to obtain the SalI insert.

In more detail, reaction 1 shows the production of a fragment containing exon 3 of CGβ and the first four amino acids of the mature α subunit as well as a SalI site 5'-ward of the coding sequences. It is obtained by amplifying a portion of the CGβ genomic sequence which is described by Matzuk, M. M. et al. *Proc Natl Acad Sci USA* (1987) 84:6354–6358; Policastro, P. et al. *J Biol Chem* (1983) 258:11492–11499.

Primer 1 provides the SalI site and has the sequence:

5'-GGA GGA AGG GTG GTC GAC CTC TCT GGT-3'.
                        SalI

The other primer, primer 2, is complementary to four codons of the α N-terminal sequence and five codons of the CGβ C-terminal sequence and has the sequence:

5'-CAC ATC AGG AGC | TTG TGG GAG GAT CGG-3'.
        ←α        | β→

The resultant amplified segment which is the product of reaction I thus has a SalI site 5'-ward of the fused coding region.

In reaction II, an analogous fused coding region is obtained from the α minigene described hereinabove. Primer 3 is a hybrid primer containing four codons of the β subunit and five codons of α and has the sequence:

5'-ATC CTC CCA CAA | GCT CCT GAT GTG CAG-3'.
        ←β        | α→

Primer 4 contains a SalI site and is complementary to the extension of α exon 4. Primer 4 has the sequence:

5'-TGA GTC GAC ATG ATA ATT CAG TGA TTG ATT-3'.
       SalI

Thus, the products of reactions I and II overlap, and when subjected to PCR in the presence of primers 1 and 4 yield the desired SalI product as shown in reaction III.

The amplified fragment containing CGβ exon 3 and the α minigene is inserted into the SalI site of pM²HA-CGβexon1,2 an expression vector which is derived from pM² containing CGβ exons 1 and 2 in the manner described by Sachais, B., Snider, R. M., Lowe, J., Krause, J. *J Biol Chem* (1993) 268:2319. pM² containing CGβ exons 1 and 2 is described in Matzuk, M. M. et al. *Proc Natl Acad USA* (1987) 84:6354–6358 and Matzuk, M. M. et al. *J Cell Biol* (1988) 106:1049–1059.

This expression vector then will produce the single-chain form human CG wherein the C-terminus of the β subunit is directly linked to the N-terminus of the α subunit.

EXAMPLE 2

Production and Activity of the Single-Chain Human CG

The expression vector constructed in Example 1 was transfected into Chinese hamster ovary (CHO) cells and production of the protein was assessed by immunoprecipitation of radiolabeled protein on SDS gels. The culture medium was collected and the bioactivity of the single-chain protein was compared to the heterodimer in a competitive binding assay with respect to the human LH receptor. In this assay, the cDNA encoding the entire human LH receptor was inserted into the expression vector pCMX (Oikawa, J. X-C et al. *Mol Endocrinol* (1991) 5:759–768). Exponentially growing 293 cells were transfected with this vector using the method of Chen, C. et al. *Mol Cell Biol* (1987) 7:2745–2752.

In the assay, the cells expressing human LH receptor ($2 \times 10^5$/tube) were incubated with 1 ng of labeled hCG in competition with the sample to be tested at 22° C. for 18 hours. The samples were then diluted 5-fold with cold Dulbecco's PBS (2 ml) supplemented with 0.1% BSA and centrifuged at 800×g for 15 minutes. The pellets were washed twice with D's PBS and radioactivity was determined with a gamma counter. Specific binding was 10–12% of the total labeled (iodinated) hCG added in the absence of sample. The decrease in label in the presence of sample measures the binding ability in the sample. In this assay, with respect to the human LH receptor in 293 cells, the wild-type hCG had an $ED_{50}$ of 0.47 ng and the single-chain protein had an $ED_{50}$ of 1.1 ng.

In an additional assay for agonist activity, stimulation of cAMP production was assessed. In this case, 293 cells expressing human LH receptors ($2 \times 10^5$/tube) were incubated with varying concentrations of the heterodimeric hCG or single-chain hCG and cultured for 18 hours. The extracellular cAMP levels were determined by specific radioimmunoassay as described by Davoren, J. B. et al. *Biol Reprod* (1985) 33:37–52. In this assay, the wild-type had an $ED_{50}$ of 0.6 ng/ml and the single-chain form had an $ED_{50}$ of 1.7 ng/ml. ($ED_{50}$ is 50% of the effective dose.)

Thus, in all cases, the behavior of both the wild-type and single-chain forms is similar.

EXAMPLE 3

Additional Activity Assays

Figure 3:
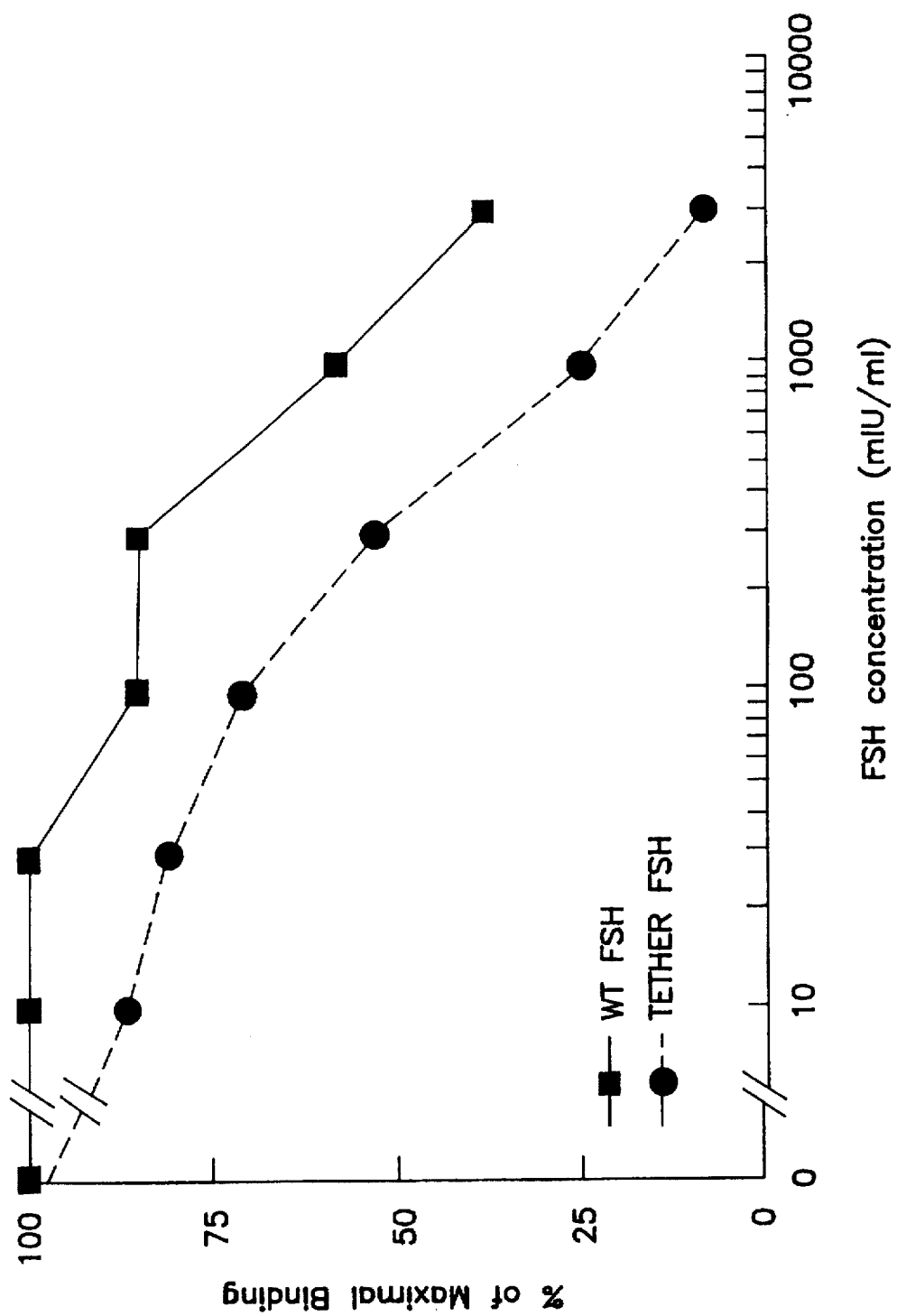
FIG. 3 shows the results of a competition binding assay for FSH receptor by various FSH analogs.

The medium from CHO cells transfected with an expression vector for the βFSH-CTP-α single-chain construct was recovered and assayed as described in Example 2. The results of the competition assay for binding to FSH receptor are shown in FIG. 3. The results indicate that the single-chain form is more effective than either wild-type FSH or FSH containing a CTP extension at the β chain in inhibiting binding of FSH itself to the receptor. The $ED_{50}$ for the single-chain form is approximately 50 mIU/ml while the $ED_{50}$ for the extended heterodimer is somewhat over 100 mIU/ml. That for wild-type FSH is about 120 mIU/ml.

Figure 4:
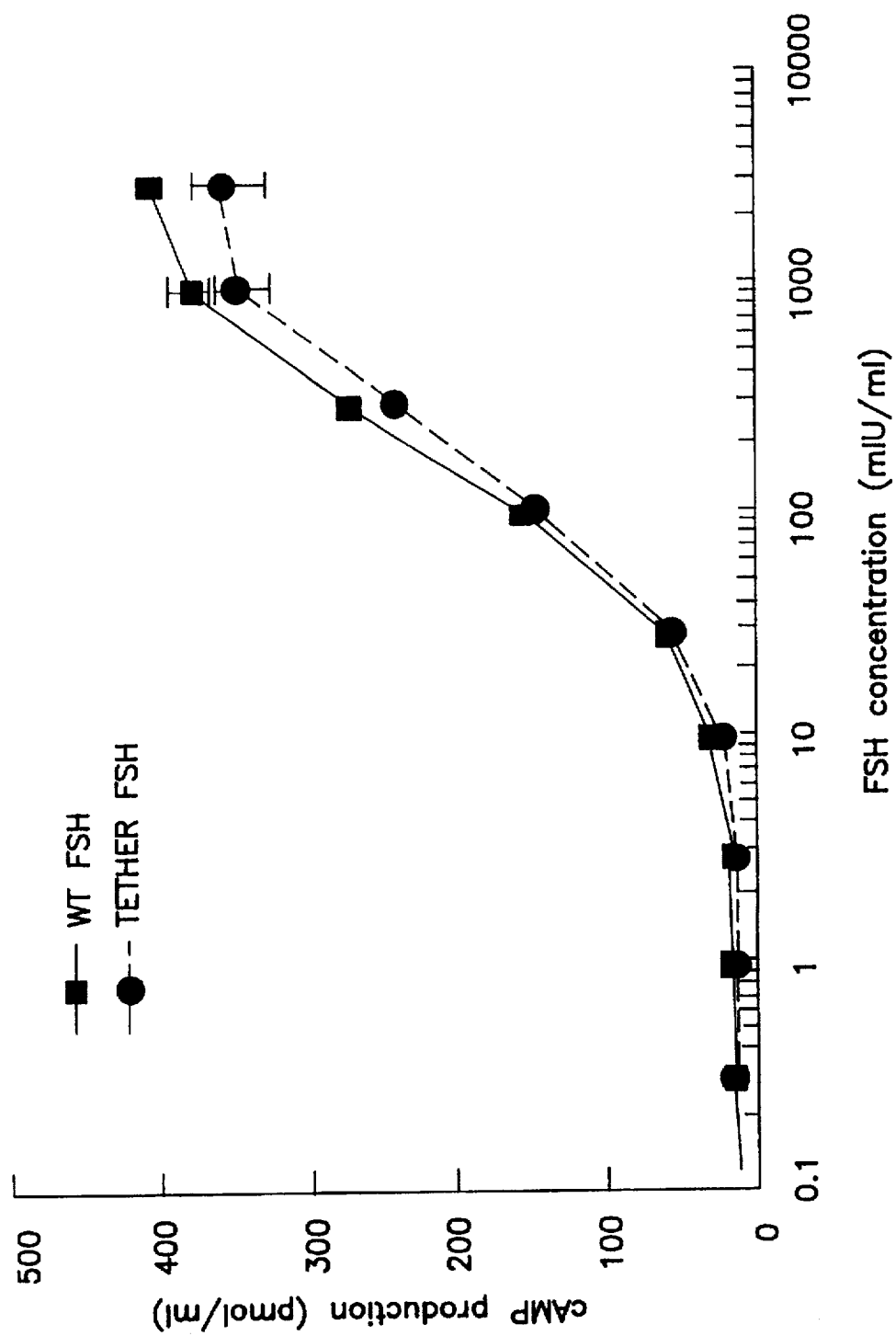
FIG. 4 shows the results of signal transduction assay with respect to FSH receptor for various FSH analogs.

The results of the signal transduction assay are shown in FIG. 4. The effectiveness of all three types of FSH is comparable.

EXAMPLE 4

Construction of Additional Expression Vectors

In a manner similar to that set forth in Example 1, expression vectors for the production of single-stranded FSH, TSH and LH (βFSH-α, βFSH-CTP-α, βTSH-α, βTSH-CTP-α, βLH-α, βLH-CTP-α) are prepared and transfected into CHO cells. The resulting hormones show activities similar to those of the wild-type form, when assayed as set forth in Example 2.

Similarly, expression vectors for the "two-β" single-chain forms are constructed in a manner analogous to that set forth in Example 1 and expressed and assayed as described in Example 2.

I claim:

1. A glycosylated or nonglycosylated single chain glycoprotein hormone antagonist of the formula

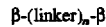

β-(linker)$_n$-β wherein each β is independently selected from the group consisting of the glycoprotein hormone β subunits FSH, TSH, LH and CG, n is 0 or 1, and "linker" is a linker moiety; and wherein:

the amino acid sequence of said first β-subunit is linked covalently through a C-terminal carboxyl or N-terminal amino group, optionally through said linker moiety, to a C-terminal carboxyl or N-terminal amino group of the amino acid sequence of said second β-subunit, wherein said β-subunits consist of the native amino acid sequences of said hormones or variants of said amino acid sequences.

2. The glycoprotein hormone antagonist of claim 1 wherein the C-terminus of one β subunit is linked covalently, optionally through a linker moiety, to the N-terminus of the other β subunit.

3. The glycoprotein hormone antagonist of claim 1 wherein said protein includes a linker moiety.

4. The single chain glycoprotein hormone antagonist of claim 1 wherein said β-subunits have the same amino acid sequence.

5. The single chain glycoprotein hormone antagonist of claim 1 wherein the β-subunits have different amino acid sequences.

6. The glycoprotein hormone antagonist of claim 3 wherein said linker comprises a complete or partial CTP unit or variant thereof.

7. The glycoprotein hormone antagonist of claim 3 wherein said linker comprises at least two CTP units or variants thereof.

8. A pharmaceutical composition which comprises the glycoprotein hormone antagonist of claim 1 in admixture with a suitable pharmaceutical excipient.

9. The glycoprotein hormone antagonist of claim 1 coupled to solid support.

10. The glycoprotein hormone antagonist of claim 3 wherein said linker comprises an amino acid or peptide.

11. The glycoprotein hormone antagonist of claim 10 wherein said linker is coupled to said β-subunits through peptide bonds.

* * * * *